United States Patent [19]

Reed et al.

[11] Patent Number: 4,493,316
[45] Date of Patent: Jan. 15, 1985

[54] ARTICULATING KNEE STABILIZER

[75] Inventors: Kenneth E. Reed; Bradley Mason, both of Carlsbad; Jeff Mason, Cardiff by the Sea; Gregory R. Nelson, Carlsbad, all of Calif.

[73] Assignee: DonJoy, Inc., Carlsbad, Calif.

[21] Appl. No.: 474,004

[22] Filed: Mar. 10, 1983

[51] Int. Cl.³ .................................................. A61F 3/00
[52] U.S. Cl. ...................................... 128/80 C; 128/88
[58] Field of Search ................. 128/80 C, 80 R, 80 F, 128/88, 87 R; 2/22, 24; 3/22, 26

[56] References Cited

U.S. PATENT DOCUMENTS

| | | | |
|---|---|---|---|
| 3,898,697 | 8/1975 | Whitehead | 128/80 C |
| 4,372,298 | 2/1983 | Lerman | 128/80 C |
| 4,381,768 | 5/1983 | Erichsen et al. | 128/80 C |

Primary Examiner—John D. Yasko
Attorney, Agent, or Firm—Albert L. Gabriel

[57] ABSTRACT

A stabilizer to support and stabilize the knee joint of the wearer having a thigh shell and calf shell formed of high impact resistant plastic. The shells are removably mountable adjacent to the knee and conform to the contours of the leg, supporting the knee joint on both sides. The shells are joined together at their lateral and medial sides by polycentric selectable arc hinge assemblies to provide support and permit controlled natural flexion and extension of the joint. Each hinge assembly has a pair of parallel links connecting corresponding sides of the shells and rotatable about pivot pins which form the points of attachment. Meshing hinge gears positioned between the links rotate with their respective shells about the pivot pins to integrate the independent rotational movement of the shells about their pivot pin axes. A pinion stop gear meshes with and is selectably rotatable about the periphery of each hinge gear. The stop gears also rotate with the hinge gears with which they mesh so that their positioning controls the allowed integrated rotation of the shells, and thus establishes the selected amount of extension and flexion of the knee stabilizer.

12 Claims, 7 Drawing Figures

U.S. Patent   Jan. 15, 1985   Sheet 1 of 2   4,493,316
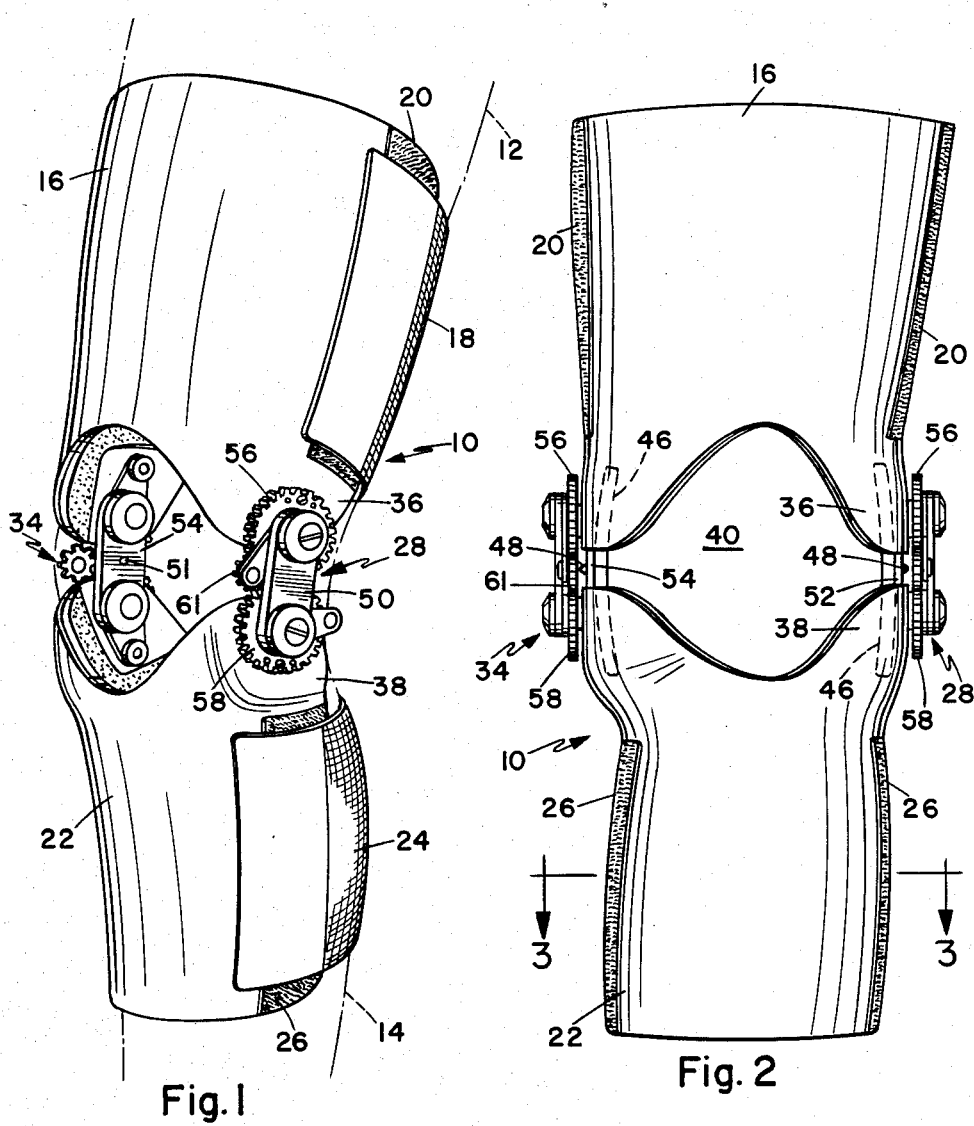
Fig. 1
Fig. 2
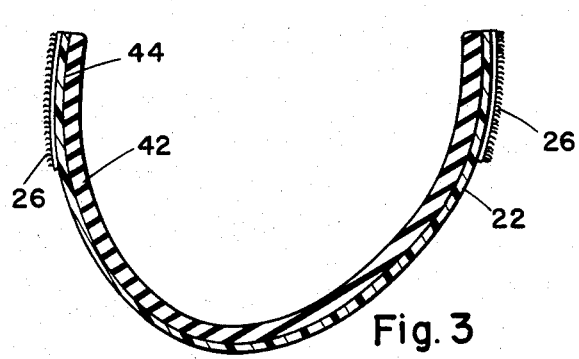
Fig. 3
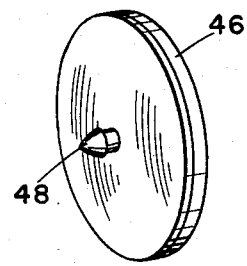
Fig. 7

ARTICULATING KNEE STABILIZER

BACKGROUND OF THE INVENTION

The present invention relates to an orthopedic support device, and particularly pertains to a polycentric knee stabilizer capable of rendering full support and stability to the knee joint at rest and in motion.

The human knee is the largest joint of the body, but due to its natural structure is the most vulnerable. The leg consists principally of a lower bone called the tibia and an upper bone known as the femur. The femur and the tibia are hinged together at the knee joint which consists of the femoral condyles supported in engagement with bearing like pads positioned on the upper end of the tibia called the medial and lateral menisci. The joint is held together by numerous ligaments, muscles and tendons, including the lateral ligaments and internal ligaments. The patella is a similarly supported bone positioned in front knee joint primarily acting as a shield for it. During flexion, the axes above which the natural movement between the tibia and femur takes place shifts backward. During extension of the knee, the axes shifts forwardly. The knee joint has a locking feature when the joint is in full extension. This latter feature permits the knee joint to be capable of supporting great weight vertically. The joint is susceptible to damage if over extended or subjected to lateral or rotational trauma. If one or more of the ligaments or other elements of the knee structure are damaged, the joint may become unstable, allowing the knee joint to wobble laterally, move forward or backward, or rotate about its generally vertical axis. Corrective surgery may also result in knee joint instability particularly during the healing process. The components of the knee joint are capable of self-healing if the joint is maintained in a suitable stable position for a proper period of time. It is also important for recovery to have the support for the healing joint elements equipped with means for permitting controlled movement when exercising the joint elements to restore their strength and natural range. It is often necessary for particular individuals, such as athletes, to continue their activity and strenuous occupations despite inherent weakness in a knee joint due to prior trauma or during recuperation. It is desirable therefore to provide support and protection to the knee joint for such persons during periods when it is subject to further injury.

Various methods and devices are available which attempt to provide such additional support and stability to the knee. Adhesive taping, resilient knee supports, or elastic bandages are used, but they provide insufficient protection. For more critical conditions, and potentially hazardous exposures, it is necessary to have stronger knee stabilizers. Available stabilizers for such purposes do not provide the requisite strength, natural motion, range, precise smooth control, and ease of adjustment needed. It is desirable that such a stabilizer cause minimal restriction to movement and be comfortable to wear. The stabilizer must be securely attached to the leg, and provide great longitudinal and lateral support in all planes, yet be capable of permitting full range of natural joint flexion and extension. For recuperative use, it is further desirable that the same device be effective in controlling the range of knee movement in flexion, extension and rotation, and be readily adjustable during use to establish and maintain the desired movement of the joint within the natural range of rotation in a manner that simulates the shifting rotational axes of a normal knee. Applicant's invention meets these and other requirements and overcomes the deficiencies of available knee stabilizers.

SUMMARY OF THE INVENTION

According to the invention, a firm fitting thigh shell and calf shell attach the stabilizer anteriorly above and below a knee joint of the wearer. The shells are made from lightweight high impact resistant plastic, and conformed to the shape of the wearer's thigh and calf. For maximum strength applications, graphite reenforced composite shells are especially advantageous. They are provided with lateral and medial extensions in way of the knee joint to support it on both sides. The interior surfaces of the shells are formed with a cushioning layer of resilient material having a textured surface bearing against the skin. The resilient layer provides for both added protection and comfort in wearing of the knee stabilizer. The shells enclose approximately one-half of the circumference of the thigh and calf and are held firmly in place by wide extensible straps attachable posteriorly between the lateral and medial sides of the shells. The form and fit of the shells to the leg cooperate with other elements of the stabilizer to prevent independent rotation of the femur and tibia.

According to the precepts of the invention, the thigh and calf shells are hingedly joined together at their lateral and medial sides adjacent to the knee joint by hinge assemblies. Each such assembly includes a pair of parallel strength links rotatably connecting corresponding sides of the shells together by means of pivot pins located at each end of the links. In addition to connecting the shells together, the links protect the hinge assemblies and provide great lateral strength for the stabilizer. Hinge gears attached to the thigh and calf shells are rotatably mounted on the pivot pins and spaced between the strength links. The teeth of the respective hinge gears mesh at the mid-length of the links. Thus, the thigh and calf shells may freely rotate about their respective pivot pin axes yet have their rotational motion integrated by the meshing of the hinge gears to simulate the polycentric axes of rotation of the natural knee joint. The meshed gears also prevent one shell from moving anteriorly or posteriorly and rotating medially or laterally in relation to the other shell. A pinion stop gear is rotatably mounted upon the periphery of each hinge gear. The stop gears are supported by arm members that are selectively rotatable about the respective hinge pivot pin axes. The stop gear teeth mesh with those of the hinge gears. Because the pinion gears rotate with the hinge gears, their selected position on the hinge gears controls the integrated rotation of the two hinge gears by permitting rotation of the latter gears unless it is stopped by the locking mesh of the teeth of one stop gear with the teeth of the opposite hinge gear. One of the pinion stop gears is selected to control the permissible flexion of the knee stabilizer, while the other stop gear controls extension.

It is an object of the invention to provide a new and improved knee stabilizer for a human knee. A stabilizer that is light in weight and comfortable to wear, while at the same time supplying great strength and stability to a knee joint against potentially damaging forces in all planes. The stabilizer permits full flexion and extension of the knee in the manner of a natural knee joint, even during strenuous activity. The stabilizer precisely and smoothly controls the degree of flexion and extension of the knee joint. Such limits may be changed by quick and easy adjustment of the stabilizer hinge mechanism without the removal of the stabilizer. The stabilizer can also accomodate a rotational misalignment between the femur and tibia of the wearer, or be adjusted to provide a torque to remedy such a condition. Because of its design and construction, the stabilizer poses minimal constraint upon the activity of a wearer while supplying maximum support.

Other objects and advantages of the invention will become apparent upon reading the following detailed description of the drawings in which like reference numerals refer to like parts throughout, and in which;

FIG. 1 is perspective view of the complete stabilizer;

FIG. 2 is a front view of the unit without the retaining straps;

FIG. 3 is an enlarged sectional view taken along line 3—3 of FIG. 2;

DETAILED DESCRIPTION OF THE DRAWINGS

Figure 4:
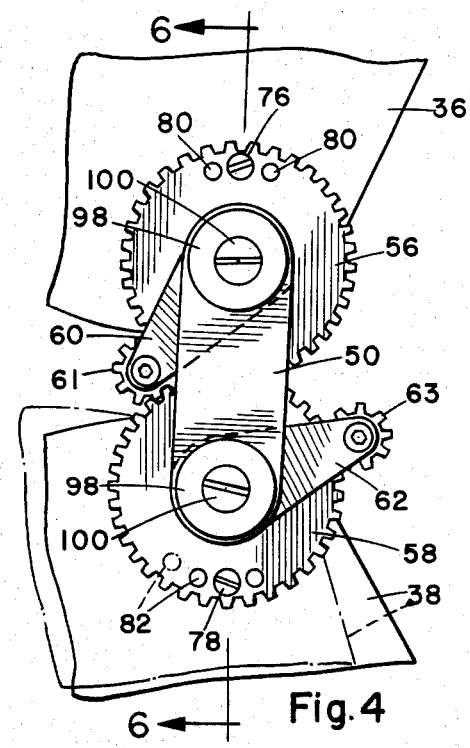
FIG. 4 is an enlarged side elevation view of the hinge connection.

The knee stabilizer 10 is illustrated in FIG. 1 as it would be attached to the thigh 12 and calf 14 of the right leg of a wearer. Thigh shell 16 is secured to the thigh 12 by extendable strap 18 employing hook and loop attachments 20 located on the lateral and medial sides of the shell 16. Calf shell 22 is similarly secured to calf 14 by means of strap 24 and hook and loop attachment 26. Hinge assembly 28 is installed on the medial side of the stabilizer joining the thigh shell 16 and the calf shell 22 by means of pivot pins 30 and 32. A lateral hinge assembly is illustrated at 34. The hinge assemblies 28 and 34 are of identical construction, but have a right and left handed orientation depending upon the side of the stabilizer 10 upon which they are mounted. The general arrangement of the hinge assemblies 28 and 34, and their principal components, are illustrated in FIGS. 1 and 2. A detailed description of a hinge assembly will be subsequently given with reference to hinge assembly 28 as being typical.

The construction of the thigh and calf shell 16 and 22 and their interconnection by the hinge assemblies 28 and 34 are illustrated in FIGS. 2 and 3. The shells are constructed of graphite composite plastic for lightweight and high impact resistance. They are formed to conform to the shape of the thigh 12 and the calf 14 of the wearer. The shells have a C-shaped configuration and are positioned anteriorly on the leg, extending approximately halfway around the thigh and calf. The thigh shell 16 has downward medial and lateral extensions 36 to support the sides of the knee joint. The calf shell 22 has upward extensions 38 for the same purpose. The opening 40 between the shell 16 and 22 is provided to accomodate the patella of the knee joint. The contour and extent of the shells is further depicted in FIG. 3 which illustrates a sectional view of the calf shell 22. To provide protection and comfort to the wearer, the interior surfaces of the shells 16 and 22 are lined with a layer of cushioning material as illustrated by the layer 42 covering the interior surface 44 of calf shell 22. In the preferred embodiment illustrated, the cushioning layer is formed of neoprene. Condyle pads 46 are removably mountable to the hinge assemblies 28 and 34 with mounting clips 48 as depicted in FIGS. 2 and 7. The pads 46 are formed of plastic and are shaped to the contours of the knee of the wearer.

Figure 5:
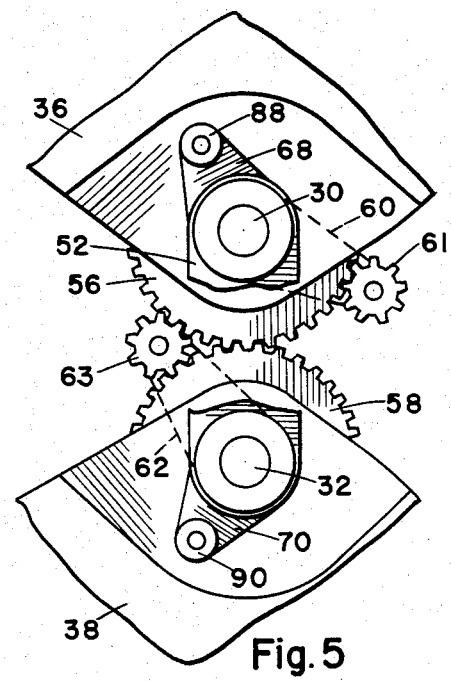
FIG. 5 is a side elevation view as seen from the inside of the stabilizer of FIG. 4, with the knee in a bent position.
Figure 6:
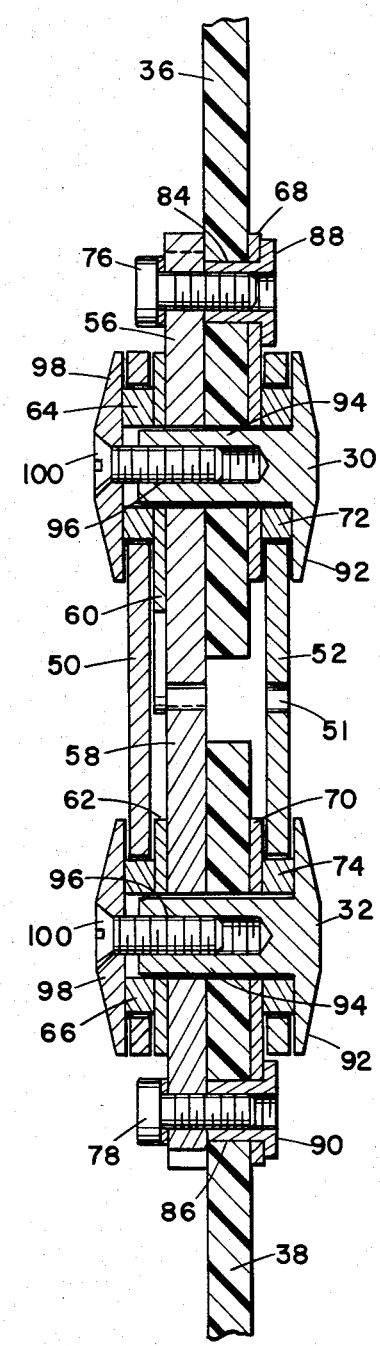
FIG. 6 is an enlarged sectional view taken on line 6—6 of FIG. 4.

The principal components of a typical hinge assembly 28 are illustrated in FIGS. 1 and 2. The hinge includes a pair of parallel stainless steel links 50 and 52. The structure and function of the interior link 52 in hinge assembly 28 can be better understoood by reference to the corresponding link 54 of hinge assembly 34 as it is depicted in FIG. 1. The links 50 and 52 are rotatably connected at their ends to the extensions 36 of thigh shell 16 and extensions 38 of calf shell 22 by pivot pins 30 and 32 respectively. The pivot pins pass through holes in the shells. Further details of the construction and assembly of typical hinge assembly 28 are illustrated in FIG. 6, and more graphically displayed in FIGS. 4 and 5. The elements of the hinge assembly 28 are contained between links 50 and 52 and are held together by pivot pins 30 and 32. The small holes 51 in the links accomodate the condyle pad mounting clips 48 (FIGS. 2 and 7). Meshing hinge gears 56 and 58, pinion stop gear arms 60 and 62 are rotatably mounted upon pivot pins 30 and 32 on the medial side of shell extension 36 and 38 between the shells and link 50. Pinion stop gears 61 and 63 are mounted at the ends of the arms 60 and 62 and mesh with the hinge gears 56 and 58. Annular bushings 64 and 66 provide bearing surfaces for the rotation of the link 50 about the axes of the pivot pins 30 and 32. The length of bushing 64 and 66 is greater than the width of ink 50 to provide working space for rotation of the link when the links are tightly drawn together by the pivot pins as will be subsequently described. Shim washers 68 and 70 are rotatably mounted on pivot pins 30 and 32 on the lateral side of the shell extensions 36 and 38 between the shells and the link 52. The shape and attachment of the washers 68 and 70 provide for better distribution of lateral stress over the shell. Lateral bushings 72 and 74 perform the same function as their opposite counterpart bushings 64 and 66.

Hinge gears 56 and 58 are also secured to the thigh shell extension 36 and the calf shell extension 38 by rotational adjustments screws 76 and 78 respectively (FIGS. 4 and 6). The adjustment screws pass through one of a series of holes 80 and 82 which are drilled in an arc through the hinge gears 56 and 58, and through a single hole 84 and 86 respectively in shell extensions 36 and 38. The shim bearing arms 68 and 70 are attached to the lateral sides of the shell by means of the screws 76 and 78. Screws 76 and 78 are held in place by being threaded into T-nuts 88 and 90.

Pivot pins 30 and 32 are T-shaped elements having broad heads 92 and shaft sections 94 which pass through the openings in shell extensions 36 and 38. The shaft sections have a threaded interior well 96. Retaining caps 98 mount upon the ends of the shaft sections, and are secured thereon by hinge locking screws 100 which are threadable into the wells 96.

As a consequence of the hinge structure and mounting the thigh shell 16, hinge gear 56, pinion stop gear arm 60, pinion stop gear 61, and shim washer 68 rotate together about pivot pin 30. Similarly, calf shell 22, hinge gear 58, pinion stop gear arm 62, pinion stop 63, and shim washer 70 rotate together about pivot pin 32. When the hinge locking screws 100 are slack, pinion stop gear arms 60 and 62 may be manually rotated about the pivot pins to selectively position stop gears 61 and 63 on the circumference of hinge gears 56 and 58. However, when locking screws 100 are fully set-up, drawing the hinge components together, the pinion stop gear arms can no longer rotate independently, and are locked in position.

Applicants' hinge design provides novel knee stabilizer features together with fineness of control through full flexion and extension not previously available. Use of two points of rotation at the ends of the steel links 50 and 52 to join the thigh shell 16 and calf shell 22 provide great lateral strength for the stabilizer. In addition, the design allows polycentric rotation between the shells, thus emulating the varying axes of rotation of a natural knee. Incorporation of the meshing hinge gears 56 and 58 which rotate with the thigh and calf shells 16 and 22 about pivot points 30 and 32 insures the maintenance of proper spacing between the shells during their movement in relation to one another, prevents the shells from moving anteriorly, posteriorly and rotationally with respect to one another and continually integrates their independent rotational motion about their respective pivot points. These latter features, together with the selectable positioning of the pinion stop gears 61 and 63 about the circumference of the hinge gears 56 and 58, allows easy and accurate control of flexion and extension in the worn stabilizer.

As illustrated by hinge assembly 28, the position of pinion stop gear 61 limits knee extension, while the position of pinion stop gear 63 controls the permitted amount of flexion. Limits of rotation are established by first manually positioning the pinion stop gears 61 and 63 on the circumference of the hinge gears 56 and 58. Gears 61 and 63 will then ride upon the hinge gears with which they mesh until they encounter and engage the teeth of the opposite hinge gear, thus preventing further rotation of the hinge. In FIG. 4 pinion stop gear 61 is illustrated in locking engagement with the calf hinge gear 58 preventing further rotational extension between the shells 16 and 22. In FIG. 5, pinion stop gear 63 is illustrated in engagement with the thigh shell gear 56 limiting flexion rotation between the thigh and calf sheels. It is apparent that the pinion stop gears 61 and 63 may be positioned to lock the stabilizer 10 in any desired position.

After design study and experimentation, the diameter and pitch of the hinge gears 56 and 58 have been selected to provide spacing for natural polycentric rotation of the knee, smooth fine control, strength, and minimal pinion stop gear profile. In the embodiment disclosed, the hinge gears 56 and 58 are 48 pitch gears having a diameter of one and one-half inches.

An additional important feature of applicants' stabilizer design is its ability to accomodate and support a knee that is rotational misaligned about the axis of the extended tibia and femur, or to induce rotation to properly align a knee that has a tendency toward misalignment. This is achieved by the ability to establish a controlled degree of rotational misalignment between the thigh shell 16 and calf shell 22 by varying the attachment positions of the hinge gears of the stabilizer as illustrated in FIG. 4. In the usual aligned stabilizer as illustrated in FIG. 1 and by the full lines in the lower half FIG. 4, the rotational adjustment screw 76 and the adjustment screw 78 are placed in the centermost of the mounting holes 80 and 82. However, as viewed from above the thigh shell, varying clockwise or counterclockwise rotational displacement between the shell 16 and the calf shell 22 may be established by the selection of an off center hinge gear mounting hole 80 and 82 on any one, or all four of the hinge gears to their respective shells. Rotation of each gear supplying one quarter of the displacement. As illustrated in FIG. 4, a clockwise rotational displacement, as viewed from above the thigh shell, has been established between shell 16 and 22. This is done by changing the attachment hole used in securing hinge gear 58 to the shell extension 38 to rotate hinge gear 58 clockwise as viewed from outside the stabilizer 10. Selection of the hole indicated results in a rotational displacement of calf shell extension 38 in relation to the thigh shell extension 36 as indicated by the broken lines of the figure. It should be recognized that the rotational misalignment capability of the stabilizer 10 would also be useful in encouraging the straightening of a misaligned joint.

OPERATION

The operation of the stabilizer 10 will be described with reference to FIGS. 1 and 2. The wearer first positions the hinge gears on one side of the stabilizer 10 to establish any rotational misalignment desired between the thigh shell 16 and calf shell 22. Next locking screws 100 are slackened, and the pinion stop gears 61 and 63 are positioned for the desired extension and flexion. The locking screws 100 are then firmly tightened to lock the pinion stop gear arms 60 and 62 in place. Similar adjustment would be made in hinge assembly 34. With condyle pads 46 in place, shells 16 and 22 are placed on the anterior of wearer's thigh and calf above and below the knee joint, and firmly secured in place with extensible straps 18 and 24 using hook and loop attachments 20 and 26. Should a change in the range of flexion or extension be desired during the wearing of stabilizer 10, it may be accomplished by merely slackening hinge locking screws 100, changing the positions of the pinion stop gears 61 and 63 and retightening the hinge locking screws 100.

Having described our invention, we claim:
1. A human knee stabilizer comprising:
   a first shell means attachable to the thigh of the wearer with a lower portion thereof disposed adjacent to at least one side of the knee joint;
   a second shell means attachable to the calf of the wearer with an upper end portion thereof disposed adjacent to at least said one side of the knee joint;
   and at least one hinge means operatively connecting said end portions of said first and second shell means on at least said one side of the knee for relative pivotal movement between said first and second shell means, said hinge means comprising:
   link means pivotally connected to said first shell means at a first pivotal connection and to said second shell means at a second pivotal connection that is spaced from said first pivotal connection,
   first and second gear means attached respectively to said first and second shell means and having meshing teeth that are actuate about the respective axes of said first and second pivotal connections, said gear means pivoting with their respective shell means, and
   a pinion stop gear adjustably positionable about the arcuate periphery of at least one of said hinge gears with the teeth of said stop gear meshed with the teeth of the hinge gear, said pinion stop gear being engageable with the teeth of the other said hinge gear to stop pivotal movement between said shells at a selected relative pivotal position of said shells.

2. A human knee stabilizer as defined in claim 1, wherein said link means comprises a pair of spaced, parallel links disposed on opposite sides of said first and second gear means.

3. A human knee stabilizer as defined in claim 2, wherein said spaced, parallel links are disposed on opposite sides of said first and second shell means.

4. A human knee stabilizer as defined in claim 1, wherein said pinion stop gear is rotateably mounted on arm means that is pivotal about the respective said axis of the said hinge gear about which it is adjustably positionable.

5. A human knee stabilizer as defined in claim 4 which comprises locking means engageable against said arm means for locking said arm means and its said pinion stop gear at a selected position on the arcuate periphery of the respective hinge gear.

6. A human knee stabilizer as defined in claim 1 which comprises a pair of said pinion stop gears, one of which is adjustably positionable about the arcuate periphery of each of said hinge gears with its teeth meshed with the teeth of the respective hinge gear, one of said pinion stop gears being positioned so as to be engageable with the teeth of the opposed hinge gear so as to control the permissible flexion of the knee stabilizer, and the other said pinion stop gear being engageable with the teeth of its opposed hinge gear so as to control extension of the knee stabilizer.

7. A human knee stabilizer as defined in claim 1 which comprises a pair of said hinge means, one of which operatively connects said end portions of said first and second shell means on one side of the knee, and the other of which operatively connects said end portions of said first and second shell means on the other side of the knee.

8. A human knee stabilizer as defined in claim 2 which comprises a pair of said hinge means, one of which operatively connects said end portions of said first and second shell means on one side of the knee, and the other of which operatively connects said end portions of said first and second shell means on the other side of the knee.

9. A human knee stabilizer as defined in claim 3 which comprises a pair of said hinge means, one of which operatively connects said end portions of said first and second shell means on one side of the knee, and the other of which operatively connects said end portions of said first and second shell means on the other side of the knee.

10. A human knee stabilizer as defined in claim 4 which comprises a pair of said hinge means, one of which operatively connects said end portions of said first and second shell means on one side of the knee, and the other of which operatively connects said end portions of said first and second shell means on the other side of the knee.

11. A human knee stabilizer as defined in claim 5 which comprises a pair of said hinge means, one of which operatively connects said end portions of said first and second shell means on one side of the knee, and the other of which operatively connects said end portions of said first and second shell means on the other side of the knee.

12. A human knee stabilizer as defined in claim 6 which comprises a pair of said hinge means, one of which operatively connects said end portions of said first and second shell means on one side of the knee, and the other of which operatively connects said end portions of said first and second shell means on the other side of the knee.

* * * * *